United States Patent [19]

Fujimaki

[11] Patent Number: 5,464,779
[45] Date of Patent: Nov. 7, 1995

[54] METHOD AND APPARATUS FOR EVALUATION OF SEMICONDUCTOR PRODUCTION PROCESS

[75] Inventor: Nobuyoshi Fujimaki, Annaka, Japan

[73] Assignee: Shin-Etsu Handotai Co., Ltd., Tokyo, Japan

[21] Appl. No.: 223,053

[22] Filed: Apr. 5, 1994

[30] Foreign Application Priority Data

Apr. 8, 1993 [JP] Japan .................... 5-107289

[51] Int. Cl.⁶ ................................ H01L 21/66
[52] U.S. Cl. .................... 437/8; 148/DIG. 162
[58] Field of Search ................ 437/8, 7; 356/30, 356/31; 148/DIG. 162

[56] References Cited

U.S. PATENT DOCUMENTS

| | | | |
|---|---|---|---|
| 4,194,127 | 3/1980 | Schmidt | 250/972 |
| 4,378,159 | 3/1983 | Galbraith | 356/237 |
| 4,899,055 | 2/1990 | Adams | 250/372 |
| 4,925,298 | 5/1990 | Dobrilla | 356/30 |
| 4,963,500 | 10/1990 | Cogan et al. | 437/8 |
| 5,198,869 | 3/1993 | Monteverde et al. | 356/30 |
| 5,233,191 | 8/1993 | Noguchi et al. | 437/8 |

OTHER PUBLICATIONS

Patent Abstracts of Japan, v16, N554 (E-1293), 25 Nov. 1992, Semiconductor Substrate, Manufacture of Semiconductor Substrate and Semiconductor . . . .

Patent Abstract of Japan, V16, N385 (E-1249), 17 Aug. 1992, Estimation Method of Semiconductor Substrate.

Jrnl of Crystal Growth, V114, N1/2, 1991 pp. 64–70, Detection and Characterisation of Microdefects and Microprecipitates in Si Wafers . . . .

Patent Abstracts of Japan, V17, N121, (E-1331), 12 Mar. 1993, Method and Device for Evaluating Semiconductor Substrate.

*Primary Examiner*—Olik Chaudhuri
*Assistant Examiner*—S. Mulpuri
*Attorney, Agent, or Firm*—Ronald R. Snider

[57] ABSTRACT

The method and apparatus of this invention for evaluation of a semiconductor production process effect the determination of the shallow pit density of a silicon wafer by predetermining the correlation between the average shallow pit density on a wafer surface obtained by microscopic observation and the average magnitude of a scattered light on the wafer surface obtained by the determination with the wafer surface inspection system operated in the haze mode, determining the average magnitude on the wafer surface of a scattered light for a silicon wafer treated by a semiconductor production process under evaluation, and analyzing the data found by the determination in combination with the correlation mentioned above. Thus, they bring about an effect of enabling the determination to be carried out automatically and quickly and exalting the accuracy of determination and allowing a generous cut in the time required for the determination as compared with the conventional determination resorting to visual measurement and evaluation.

3 Claims, 5 Drawing Sheets

5,464,779

METHOD AND APPARATUS FOR EVALUATION OF SEMICONDUCTOR PRODUCTION PROCESS

BACKGROUND OF THE INVENTION

1. Field of the Invention

This invention relates to a method for the evaluation of a semiconductor production process and more particularly to a method for the determination of a shallow pit density on a surface of a silicon wafer, an apparatus for the determination of a shallow pit density on a surface of a silicon wafer, and a method for the evaluation of cleanliness of a heat-treating furnace or accessorial devices thereof.

2. Prior Art Statement

In a process for the production of a semiconductor device, a silicon wafer is subjected to a thermal oxidation treatment for the formation of an oxide film and a thermal diffusion treatment for the diffusion of dopant impurities. An oxidizing furnace and a diffusing furnace are used as devices for these treatments.

For the purpose of producing semiconductor devices at a highly satisfactory yield, it is extremely important to manage a process and apparatus for the production lest metallic and other pollutants should adhere to the surfaces of silicon wafers and further diffuse in the silicon wafers.

When heavy metals (Cu, Ni, Fe, etc.) are present on or within the component members of the production apparatus, however, they precipitate the silicides such as of Ni and/or Cu in the form of clusters of minute defects on the surfaces of silicon wafers during the heat treatment and generate a visually discernible haze (extremely minute rises and falls of wafer surface). There are also times when these heavy metals form nucleations and generate stacking faults. When the silicon wafers generate such crystal defects as hazes and stacking faults, these crystal defects degrade the mechanical and electrical properties of the silicon wafers and entail a problem of lowering of the yield.

The maintenance of such heat-treating furnaces as oxidation furnaces in a state of high cleanliness, therefore, is important from the point of view of preventing the problem mentioned above. Thus, the necessity of establishing a technique for accurate evaluation of this cleanliness is finding recognition.

As means for this evaluation, JP-B-5-2,937 discloses a method which comprises heat-treating a silicon wafer with a heat-treating furnace in an oxidizing atmosphere, preferentially etching the heat-treated silicon wafer and microscopically observing shallow pits consequently formed on the etched surface thereof, and determining the shallow pit density by visually counting the number of shallow pits.

As a apparatus capable of automatically rating such pits on a silicon wafer as shallow pits by means of an optical instrument, a wafer surface inspection system has been known in the art (for further information, refer to the March, 1986 issue of "Monthly Semiconductor World," pp. 109 to 115 or the July, 1986 issue of "Nikkei Microdevices," pp. 165 to 170). These reports indicate that cross-sectional areas or sizes of pits found with a laser beam are totally useless for the determination of shallow pit density unless depths of such pits are also found.

This method of quantitative determination of shallow pit density requires skill on the part of an operator and, more often than not, the data obtained thereby widely vary from one operator to another. This method, therefore, is at a disadvantage in attaining highly reliable determination only with difficulty at the cost of time and labor.

If the time required for the determination with the wafer surface inspection system is shortened somehow, the uncertainty of the relation between the shallow pit density determined by the microscopic observation which consumes time, labor and demands skill and the magnitude of scattered light (the quotient of the intensity of scattered light divided by the intensity of incident light) determined by the inspection system mentioned above still poses a problem.

SUMMARY OF THE INVENTION

This invention, produced by the urge to solve the problem mentioned above, has for its object the provision of a method for determining the shallow pit density conveniently and quickly with high accuracy, and a method and apparatus for evaluating the cleanliness such as of an oxidation furnace mentioned above based on this method of determination and the realization of accurate evaluation of a semiconductor production process.

The first aspect of this invention resides in a method for the evaluation of a semiconductor production process by the examination of a silicon wafer obtained after the step of heat treatment in an oxidizing atmosphere and the step of preferential etching of the said heat treated silicon wafer, which method is characterized by obtaining preparatorily the correlation between the average value of a shallow pit dinsity on the surface of said wafer by the microscopic observation and the average value of the magnitude of scattered light caused on said wafer surface by the shallow pits (the quotient of the intensity of scattered light divided by the intensity of incident light) determined with a wafer surface inspection system using a beam of light, determining the average value of the magnitude of scattered light caused on the surface of a silicon wafer under examination by the use of said wafer surface inspection system, and determining the shallow pit density of said silicon wafer under examination based on said average value of the magnitude of scattered light on said wafer surface and said correlation.

Second aspect of this invention reside in an apparatus for the evaluation of a semiconductor production process by the use of a wafer surface inspection system using a beam of light, which apparatus is characterized by the fact that said wafer surface inspection system is provided with detection means capable of adjusting the sensitivity of inspection proportionately to the magnitude of scattered light caused by shallow pits on the surface of a silicon wafer.

The third aspect of this invention resides in a method for the evaluation of a semiconductor production process by the inspection of the cleanliness of a heat-treating furnace for a silicon wafer or an accessorial device of said furnace being oparated in said semiconductor production process, which method is characterized by the fact that the cleanliness of said heat-treating furnace or said accessorial device therefor is judged for acceptability or rejectability based on the density of shallow pits on the surface of a silicon wafer determined by the use of the apparatus for evaluation set forth in the second aspect of this invention in accordance with the method set forth in the first aspect of this invention.

BRIEF DESCRIPTION OF THE DRAWINGS

The invention will be better understood and the objects and features thereof other than those set forth above will become apparent when consideration is given to the following detailed description thereof, which makes reference to the annexed drawings wherein.

DETAILED DESCRIPTION OF THE INVENTION

Figure 1:
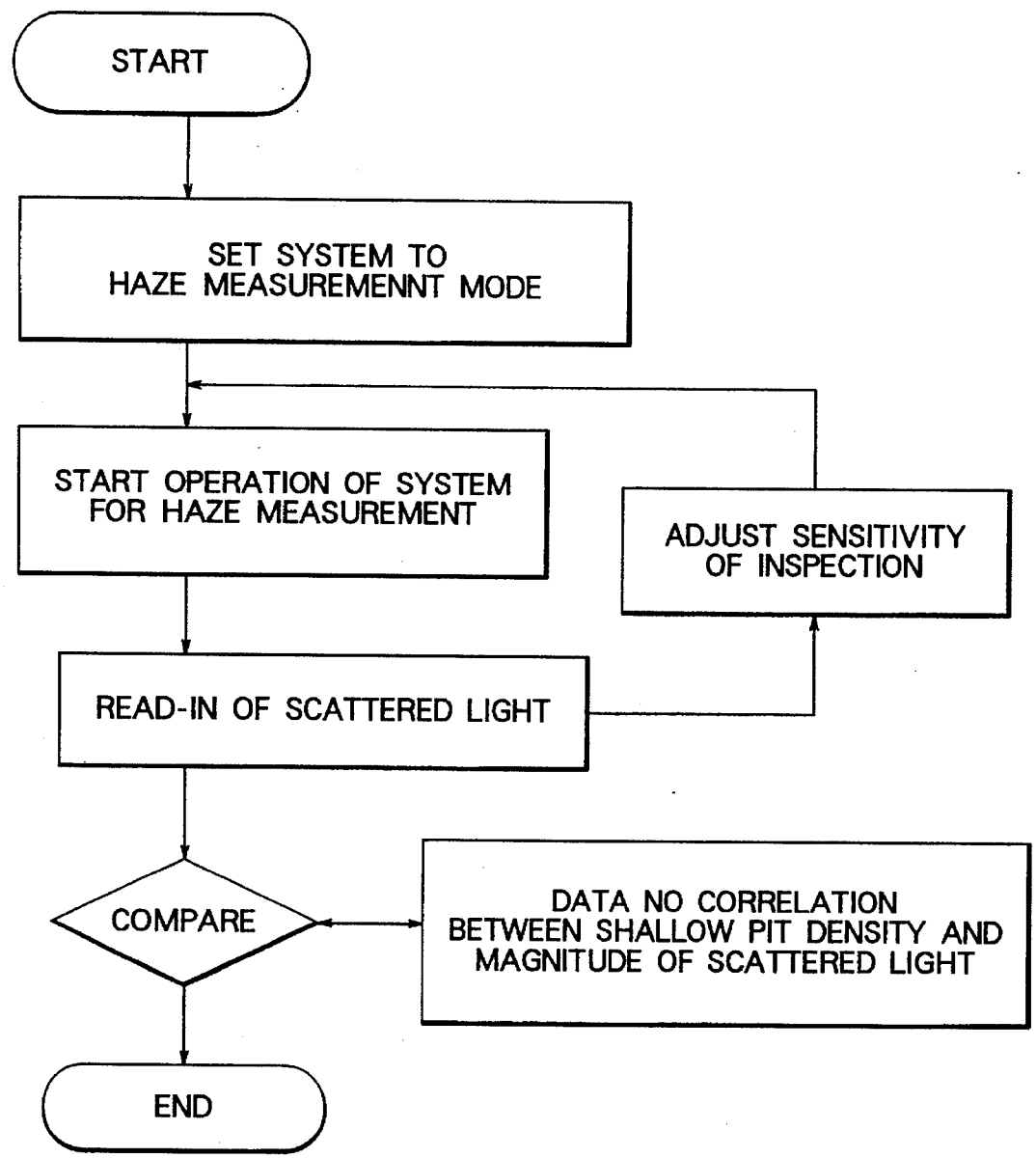
FIG. 1 is a flow chart for aiding in the description of the operation of a wafer surface inspection system for the determination of a shallow pit density.

The wafer surface inspection system is generally designed to count particles (dust) adhering to the surface of a silicon wafer. This system operates on the principle of repeating a linear scanning at a constant period with a laser beam, moving a silicon wafer in a direction perpendicular to the direction of the scanning and effecting the scanning throughout the entire surface of the silicon wafer, determining the cross section of scattering (the quotient of the intensity of a scattered light divided by the intensity of an incident light, generally expressed by the denomination of $\mu m^2$) based on the intensity of a scattered light emitted from a particle on the surface of the silicon wafer and meanwhile comparing the results of the determination, and rendering a decision "one particle is present" when the cross section of scattering reaches the maximum in the direction of scanning of the laser beam and in the direction perpendicular thereto.

This system has a capability to set and switch the determination mode as to determine selectively a scratch or a glossy defect of a size larger than the wavelength of a laser beam, an isolate particle of a size equal to or smaller than the wavelength, or a haze of a size far smaller than the wavelength over a large portion of the wafer surface.

The result of the determination by this system is displayed together with an image of the silicon wafer on the CRT. This image is processed with a computer and, as a result, the average cross section of scattering on the surface of the silicon wafer, the histogram of the cross section of scattering and the number of particles, the maximum cross section of scattering, and the positions of scattering are printed out in the form of a map output. (The foregoing description on the operation of the wafer surface inspection system is based on the information published in the July, 1986 issue of "Nikkei Microdevices," pp. 165 to 170.)

The shallow pits involved in this invention are a group of extremely minute pits different from the aforementioned haze which consists of extremely minute rises and falls on the wafer surface. They, however, belong to the category of haze as sorted for the sake of the mode of determination mentioned above. By setting the silicon wafer surface inspection system mentioned above to the mode of determination of haze, therefore, the shallow pits can be quantified.

Incidentally, the magnitude of a scattered light caused by a haze is generally expressed by the ratio thereof to the intensity of an incident light. In case the intensity of scattered light is one millionth based on the intensity of the incident light taken as unity (1), for example, the magnitude of the scattered light is expressed as 1 ppm.

On a silicon wafer which has a high shallow pit density or etch pit density, however, not only the number of pits but also the degree of rises and falls of the silicon wafer surface is increased. Since the pits generated with pollutants of heavy metal cannot be selectively determined apart from the other pits, the exact shallow pit density is quantified only with difficulty. Further, because of the synergism of the pits with the rises and falls of wafer surface, the number of data required for the determination far exceeds that of data which can be processed simultaneously by the computer. The mapping to be consequently produced is imperfect because of a missing part and does not permit observation of the entire surface of the wafer. (Even if the capacity for data processing is increased somehow, this increase has its own limit. If the problem of capacity of the data processing is solved at all, this solution entails a notable decrease in the speed of image processing possibly to the extent of rendering the determination itself impracticable.)

The apparatus for evaluation which is set forth in the second aspect of this invention is intended to solve this problem. To be specific, for the purpose of excluding the scattering due to the rises and falls of the wafer surface thereby securing the information exclusively of the pits, this apparatus is adapted to continue the determination while simultaneously detecting a change in the sensitivity of inspection depending on the existent shallow pit density.

Then, the apparatus establishes a correlation between the average magnitude of a scattered light on the surface of a wafer determined by the aforementioned apparatus for evaluation and the average shallow pit density on the surface of the wafer found by the microscopic observation and, based on this correlation, effects automatic quantification of the shallow pit density.

[Examples]

Now, this invention will be described more specifically below with reference to working examples of the invention.

Example 1

First, the procedure for establishing the relation between the average shallow pit density on the surface of a wafer and the average of the magnitude of a scattered light on the surface of the wafer will be demonstrated.

The silicon wafer was an N type <100> wafer and 5 inches in diameter which was obtained by the FZ method and polished to a mirror finish and had a resistivity in the range of 1 to 100 Ω cm. This wafer was set in place in a heat-treating furnace and heat-treated in a wet oxygen atmosphere at 1,150° C. for 100 minutes. The heat-treated silicon wafer was etched with an etchant (a 1:2 mixture of aqueous (0.15 mol %) dichromic acid solution: aqueous (50%) hydrofluoric acid solution; marketed under a trademark designation of "Secco Solution") for one minute.

In this case, for the purpose of obtaining silicon wafer samples having varying shallow pit densities, the heat-treating furnace used for the heat treatment was operated under varying conditions ranging from the condition of high cleanliness obtained as by cleaning or baking under no load to the condition of heavy pollution due to frequent use.

As a result, silicon wafer samples having six different levels of shallow pit density were obtained.

The samples were subjected to microscopic observation and to examination with the wafer surface inspection system. The results are shown below.

Figure 2:
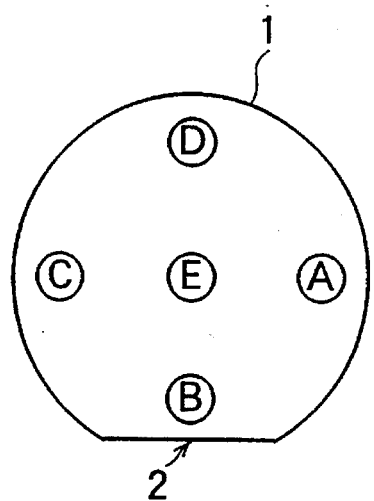
FIG. 2 is an explanatory diagram illustrating points for determination of a shallow pit density by microscopic observation in Example 1.

In the microscopic observation at 500 magnifications, the shallow pit density was visually measured at five points, namely the points A, B, C, and D in the peripheral part and the central point E, on the surface of a silicon wafer illustrated in FIG. 2 and the average of the values obtained at the five points was reported as the average shallow pit density on the wafer surface. The measurement could be obtained with high accuracy if the observation was performed throughout the entire surface of the silicon wafer. This measurement, however, would call for enormous amounts of time and labor, and would be hardly necessary. And so the observation at the five points mentioned above was judged to suffice to effect the determination under discussion. In the diagram of FIG. 2, the reference numeral 2 stands for an orientation flat.

Figure 3:
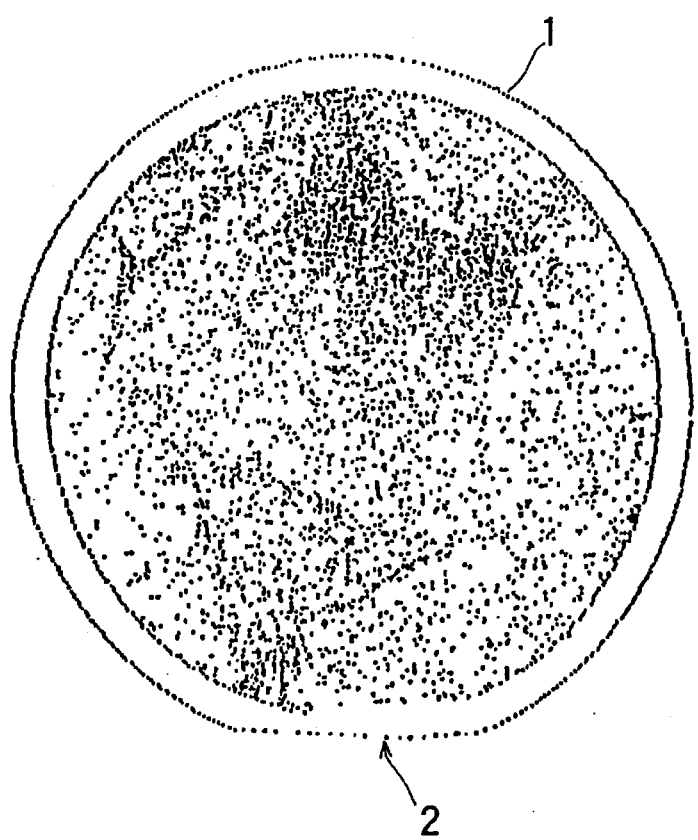
FIG. 3 is one example of the image of a silicon wafer displayed on the CRT in Example 1.

In the wafer surface inspection system, the apparatus for inspection was set to the haze mode as illustrated in FIG. 1. The read-in of a scattered light was continued while separating and removing the rises and falls from the shallow pits by adjusting the sensitivity of inspection according to the shallow pit density. As a result, a mapping substantially equal to the pattern observable by spotlight illumination was obtained as illustrated in FIG. 3.

Figure 4:
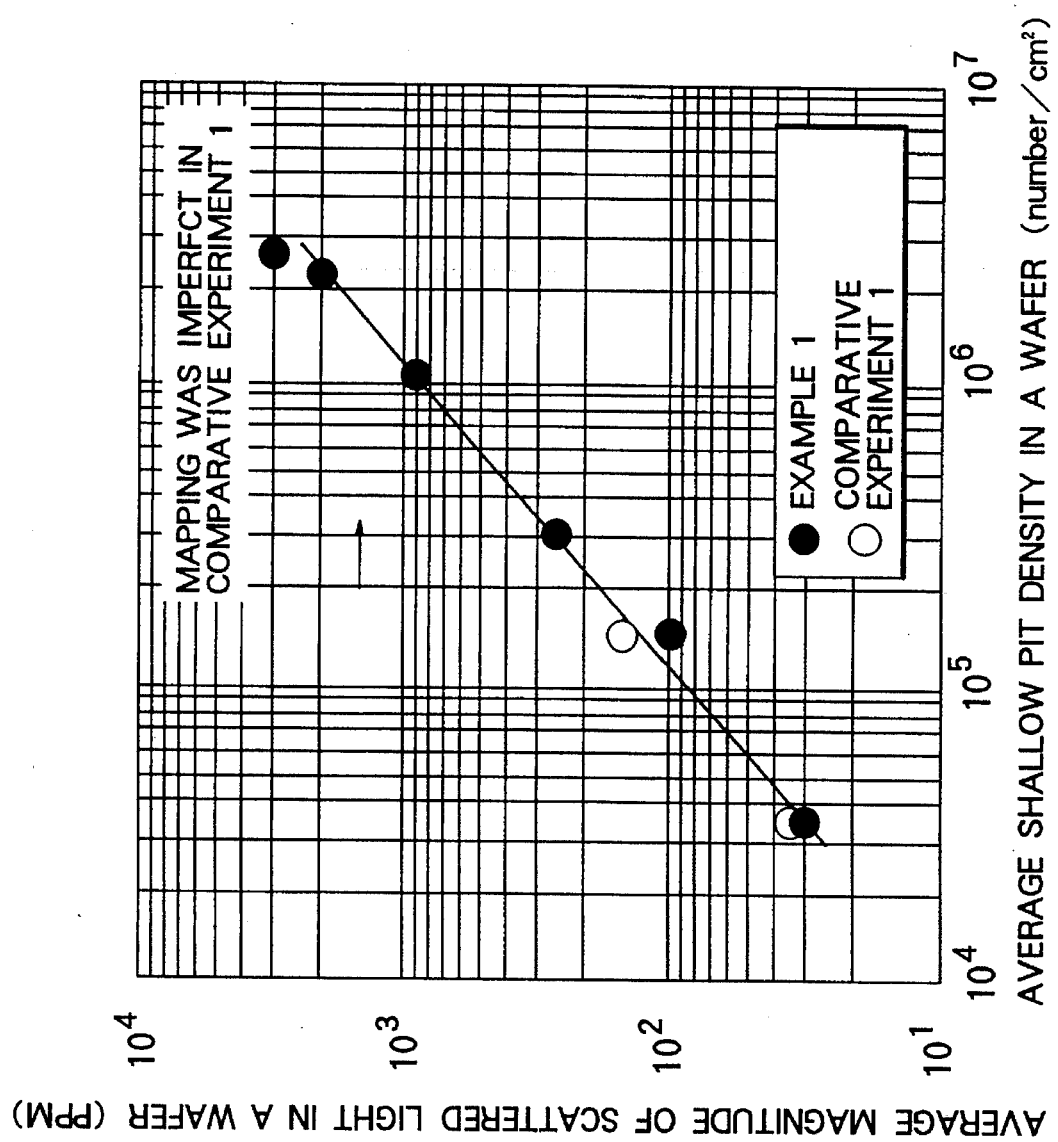
FIG. 4 is a graph showing the relation between the average value of shallow pit density on a wafer surface and the average value of the magnitude of scattered light on a wafer surface obtained in Example 1 and Comparative Experiment 1.

The relation between the average shallow pit density on the surface of wafer obtained by the microscopic observation and the average magnitude of a scattered light on the wafer surface obtained by the wafer surface inspection system was as shown in FIG. 4 (indicated with closed marks ● in the diagram). It was a strongly positive correlation.

It is clearly noted from the relation shown in FIG. 4 that the use of the wafer surface inspection system in accordance with this invention permits automatic determination of the shallow pit density. Thus, the evaluation of a semiconductor production process can be attained on the basis of this correlation.

Example 2

Silicon wafers treated in a semiconductor production process were investigated to determine the degree with which the shallow pit density of the silicon wafer affected device characteristics.

Each silicon wafer used herein was manufactured and treated in the same batch that afforded the silicon wafer samples with six levels as used in Example 1. It was not subjected to the preferential etching.

The manufacture of this silicon wafer into an MOS diode was carried out by cleaning this silicon wafer through removal of an oxide film from the surface thereof, then forming a gate oxide film 50 nm in thickness by a heat treatment at 1,000° C. for 60 minutes in a dry oxygen atmosphere and an aluminum electrode 1 μm in thickness by the vacuum deposition method, removing the oxide film from the reverse side of the silicon wafer, and subsequently heat-treating the resultant composite in an atmosphere of a hydrogen-nitrogen mixture (hydrogen content 3%) at 400° C. for 30 minutes.

Figure 5:
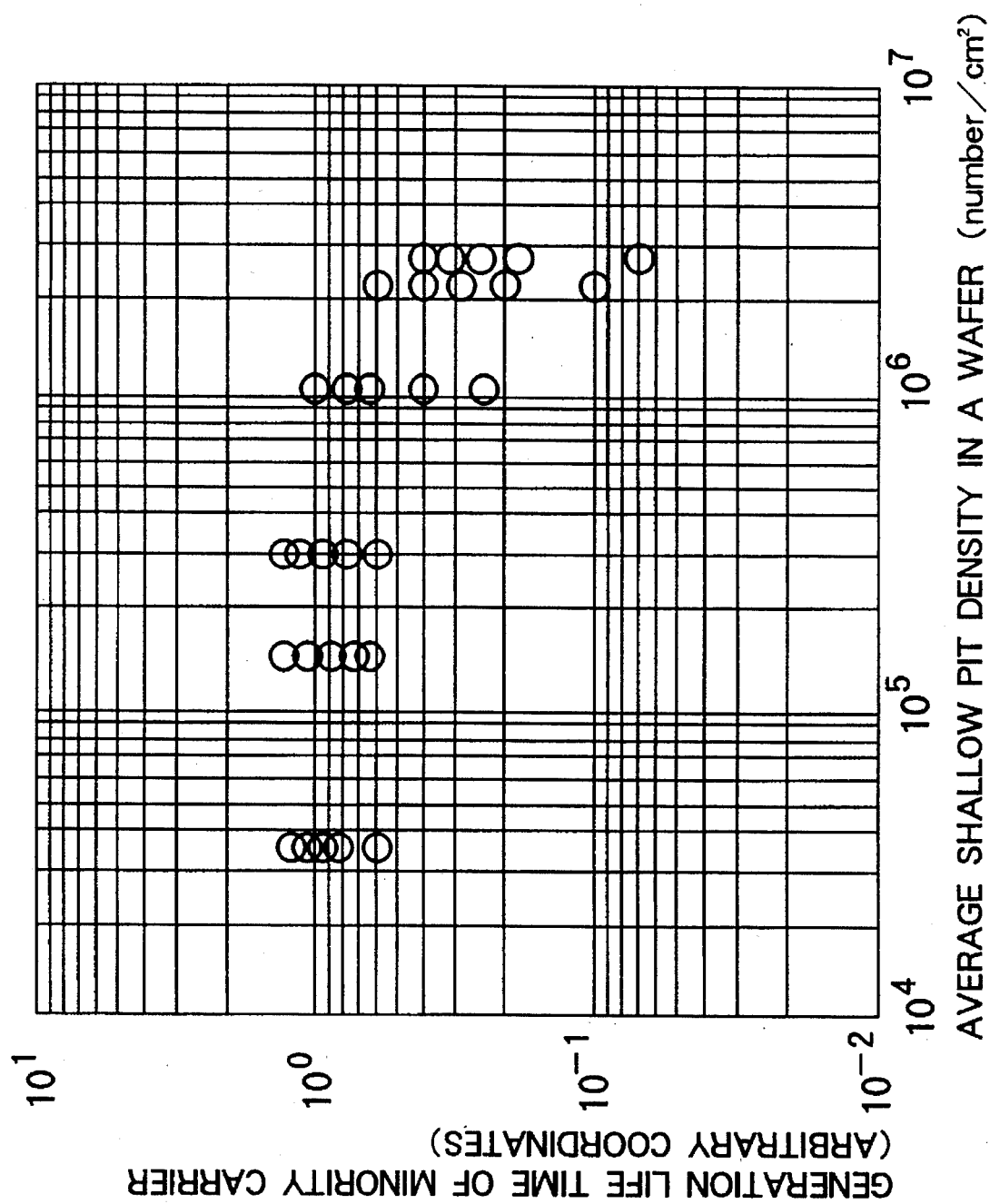
FIG. 5 is a graph showing the relation between the average value of shallow pit density on a wafer surface and the generation life time of a minority carrier obtained in Example 2.

The relation between the average shallow pit density on the wafer surface and the generation life time, τg, of a minority carrier by the MOS C-t method is shown in FIG. 5. In this case, the silicon wafers were each tested for the C-t characteristics at the five points shown in FIG. 2. The results were standardized by using the average generation life time of minority carrier of the wafer having the lowest shallow pit density taken as unity (1). The results are graphically shown in FIG. 5.

It is clearly noted from the results that the dispersion of the generation life time τg increased and, at the same time, the absolute value of the life time τg decreased when the average of the shallow pit density on the wafer surface exceeded $1.05 \times 10^6/cm^2$. Further, the value of τg showed virtually no change in spite of the change of the shallow pit density indicating of the degree of cleanliness over a wide range from $10^4$ to 106. This fact suggests that the method of evaluation of a semiconductor production process by the determination of the shallow pit density quite excels in sensitivity.

Separately, the oxide film formed on the silicon wafer was also tested for fixed charge and mobile ion (alkaline metal ion) by the C-V method. The test results showed no relation with the shallow pit density.

From the results indicated above, it is clearly noted that the method for evaluation of a semiconductor production process by the determination of the shallow pit density conspicuously excels in sensitivity as compared with the method which effects the evaluation by the determination of device characteristics, for example the aforementioned MOS diode characteristics.

Since the shallow pit density which affects the genaration life time τg of a minority carrier determined by the MOS C-t method is considered to be above the level of about $5 \times 10^5/cm^2$ as described above, it is reasonable to rate a semiconductor production process as acceptable when the shallow pit density of the silicon wafer produced by this process is below $4 \times 10^6/cm^2$.

Comparative Experiment 1

The same silicon wafers with six levels as used in Example 1 were used herein.

The wafer surface inspection system was set to the haze mode of determination and the sensitivity of determination was fixed without reference to the shallow pit density to carry out the determination without removing the rises and falls of the wafer surface.

As a result, in a silicon wafer having a high shallow pit density (equivalent to a magnitude of scattered light exceeding 252 ppm), exact quantification of the shallow pit density could not be obtained because not only the degree of pits but also that of rises and falls of the silicon wafer surface increased and the selective determination of the pits generated by pollutants of heavy metal was not attained.

Figure 6:
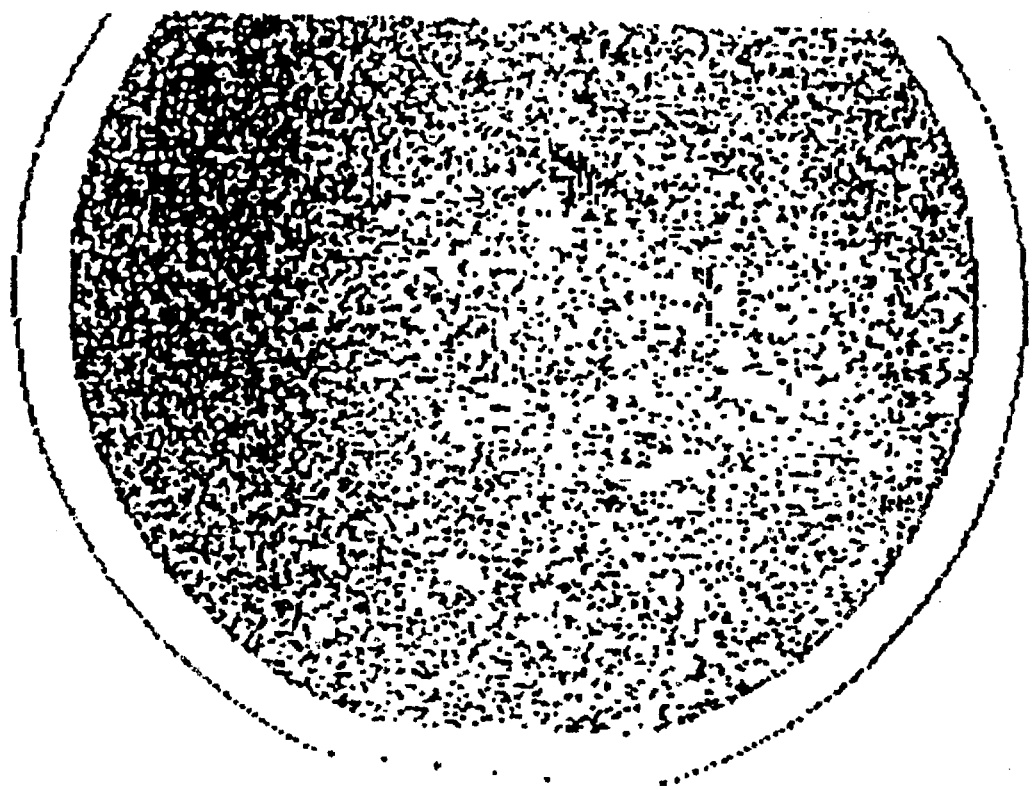
FIG. 6 is one example of the image of a silicon wafer displayed on the CRT in Comparative Experiment 1.

Further, because the number of data far exceeded the number of data capable of being simultaneously processed with a computer, the produced mapping was imperfect because of a missing part as illustrated in FIG. 6 and the desired observation of the whole surface of a wafer was not attained. If the capacity for data processing is increased, this increase has its own limit. If the problem of the capacity for data processing is solved somehow, the solution entails an extreme decrease in the speed of image processing. The method of this comparative experiment, therefore, is impracticable for the purpose of the determination under discussion.

The relation between the average shallow pit density on the wafer surface determined by the microscopic observation and the average magnitude of a scattered light on the wafer surface determined by the wafer surface inspection system, obtained in this comparative experiment is shown in FIG. 4 (indicated with open marks ○ in the diagram). The results clearly indicate that no correlation was obtained when the shallow pit density was high, while a positive correlation was obtained when the shallow pit density was low.

As described above, the method for evaluation of a semiconductor production process which is set forth in the first aspect of this invention herein and the apparatus for evaluation of a semiconductor production process which is set forth in the second aspect of this invention herein effect the determination of the shallow pit density of a silicon wafer by predetermining the correlation between the average shallow pit density on a wafer surface obtained by microscopic observation and the average magnitude of a scattered light on the wafer surface obtained by the determination with the wafer surface inspection system operated in the haze mode, determining the average magnitude on the wafer surface of a scattered light of a silicon wafer treated by a semiconductor production process under evaluation, and analyzing the data found by the determination in combination with the correlation mentioned above. Thus, they bring about an effect of enabling the determination to be carried out automatically and quickly and exalting the accuracy of determination and allowing a generous cut in the time required for the determination as compared with the conventional determination resorting to visual measurement and evaluation.

The method for evaluation of a semiconductor production process which is set forth in the third aspect of this invention herein effects the judgment of acceptance/rejection of a semiconductor production process on the basis of the shallow pit density of a silicon wafer which has undergone the treatment in the semiconductor production process. Thus, it brings about an effect of attaining the evaluation with high quality and extremely high sensitivity as compared with the conventional method which relies for evaluation on the determination of device characteristics such as, for example, the aforementioned MOS diode characteristics.

While there have been shown and described preferred embodiments of the invention, it is to be distinctly understood that the invention is not limited thereto but may be otherwise embodied and practiced variously within the scope of the following claims.

What is claimed is:

1. A method for the evaluation of a semiconductor production process, comprising the steps of:

heat-treating a silicon wafer by using a furnace system and etching the heat-treated silicon wafer by immersing in an etching liquid;

obtaining a correlation between an average value of shallow pit density determined by microscopic observation and an average value of a magnitude of light scattered determined by a wafer surface inspection system using a beam of light, which correlation is characterized by obtaining several heat-treated silicon wafers by using furnace systems with different levels of impurity contamination;

determining an average value of the magnitude of scattered light reflected from a surface of a silicon wafer by using said wafer surface inspection system, which wafer is heat-treated by a furnace system under evaluation;

determining the shallow pit density of said heat-treated silicon wafer from said furnace system under evaluation, based on said average value of the magnitude of scattered light reflected from said silicon wafer surface and said correlation;

inspecting the cleanliness of said furnace system for heat treating the silicon wafer in the semiconductor production process; and judging the acceptability or rejectability of said furnace system, based on said determining of shallow pit density.

2. A method according to claim 1, wherein the judgement of the acceptability is below $4 \times 10^5/cm^2$ of the shallow pit density.

3. A method according to claim 1, wherein said silicon wafer obtained by FZ method is an N type <100>, having resistivity in the range of 1 to 100Ω cm.

* * * * *